(12) United States Patent
Cas et al.

(10) Patent No.: US 9,301,068 B2
(45) Date of Patent: Mar. 29, 2016

(54) ACOUSTIC PRESCRIPTION RULE BASED ON AN IN SITU MEASURED DYNAMIC RANGE

(75) Inventors: Erwin Cas, Wuustwezel (BE); Mark C. Flynn, Gothenburg (SE); Christopher J. James, Toulouse (FR)

(73) Assignee: Cochlear Limited, Macquarie University (AU)

( * ) Notice: Subject to any disclaimer, the term of this patent is extended or adjusted under 35 U.S.C. 154(b) by 468 days.

(21) Appl. No.: 13/276,723

(22) Filed: Oct. 19, 2011

(65) Prior Publication Data

US 2013/0102923 A1 Apr. 25, 2013

(51) Int. Cl.
*A61B 5/00* (2006.01)
*H04R 25/00* (2006.01)
*A61B 5/12* (2006.01)

(52) U.S. Cl.
CPC ............... *H04R 25/70* (2013.01); *A61B 5/123* (2013.01)

(58) Field of Classification Search
CPC ........... A61B 5/121; A61B 5/12; H04R 25/70
USPC ............... 600/559, 25; 607/57; 381/312, 314; 2/559
See application file for complete search history.

(56) References Cited

U.S. PATENT DOCUMENTS

| | | | |
|---|---|---|---|
| 4,548,082 A | | 10/1985 | Engebretson et al. |
| 5,553,151 A | * | 9/1996 | Goldberg ...................... 381/312 |
| 6,654,594 B1 | * | 11/2003 | Hughes et al. .............. 455/245.1 |
| 6,731,767 B1 | * | 5/2004 | Blamey et al. ................ 381/312 |
| 7,068,793 B2 | | 6/2006 | Shim |
| 7,634,400 B2 | * | 12/2009 | Averty et al. ................. 704/205 |
| 7,650,004 B2 | * | 1/2010 | Durant .......................... 381/312 |
| 2005/0078842 A1 | | 4/2005 | Vonlanthen et al. |
| 2005/0111683 A1 | * | 5/2005 | Chabries et al. .............. 381/317 |

(Continued)

FOREIGN PATENT DOCUMENTS

| | | |
|---|---|---|
| EP | 0844805 A1 | 5/1998 |
| KR | 10-2001-0008008 A | 2/2001 |

(Continued)

OTHER PUBLICATIONS

International Search Report and Written Opinion of International Application No. PCT/IB2012/055755 dated Mar. 20, 2013 (mailed Mar. 25, 2013).

(Continued)

*Primary Examiner* — Sean Dougherty
*Assistant Examiner* — Daniel Cerioni
(74) *Attorney, Agent, or Firm* — McDonnell Boehnen Hulbert & Berghoff LLP

(57) ABSTRACT

The present application discloses systems, methods, and articles of manufacture for determining prescription rules for a hearing prosthesis. A method in accordance with the present disclosure includes identifying a threshold hearing level and an uncomfortable loudness level for a channel of a hearing prosthesis. In one example, the threshold hearing level and the uncomfortable loudness level are determined in response to a stimulation signal generated utilizing the hearing prosthesis in situ on a recipient. In the present example, the stimulation signal corresponds to the channel of the hearing prosthesis. The method further includes developing a prescription rule based on the threshold hearing level and the uncomfortable loudness level. Generally, the prescription rule includes at least one of a linear compression scheme and a wide dynamic range compression scheme.

18 Claims, 5 Drawing Sheets

(56) References Cited

U.S. PATENT DOCUMENTS

| | | |
|---|---|---|
| 2005/0141733 A1* | 6/2005 | Blamey et al. ............... 381/312 |
| 2007/0027676 A1* | 2/2007 | Chambers et al. ......... 704/200.1 |
| 2007/0172088 A1* | 7/2007 | Olsen et al. .................. 381/312 |
| 2009/0136050 A1 | 5/2009 | Hakansson et al. |
| 2009/0138062 A1 | 5/2009 | Balslev |
| 2009/0306458 A1 | 12/2009 | Parker et al. |
| 2010/0290654 A1 | 11/2010 | Wiggins et al. |
| 2011/0270014 A1* | 11/2011 | Flynn et al. .................... 600/25 |
| 2012/0004705 A1* | 1/2012 | James ............................ 607/57 |
| 2013/0006042 A1* | 1/2013 | Hillbratt et al. ................ 600/25 |

FOREIGN PATENT DOCUMENTS

| | | |
|---|---|---|
| WO | 2009124010 A2 | 10/2009 |
| WO | 2010017579 A1 | 2/2010 |

OTHER PUBLICATIONS

Dillon, Hearing Aids, Prescribing Hearing Aid Performance, Section 9.3.6, 2001, pp. 254-255, Boomerang Press, Sydney, Australia.

* cited by examiner

ACOUSTIC PRESCRIPTION RULE BASED ON AN IN SITU MEASURED DYNAMIC RANGE

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound directly or indirectly to a person's bone or teeth, thereby causing vibrations in the person's inner ear and bypassing the person's auditory canal and middle ear. Vibration-based hearing devices include, for example, bone anchored devices, direct acoustic cochlear stimulation devices, or other vibration-based devices. A bone-anchored device typically utilizes a surgically implanted mechanism or a passive connection through the skin or teeth to transmit vibrations corresponding to sound via the skull. A direct acoustic cochlear stimulation device also typically utilizes a surgically implanted mechanism to transmit vibrations corresponding to sound, but bypasses the skull and more directly stimulates the inner ear. Other non-surgical vibration-based hearing devices may use similar vibration mechanisms to transmit sound via direct or indirect vibration of teeth or other cranial or facial bones.

Persons with certain forms of sensorineural hearing loss may benefit from prostheses, such as cochlear implants and/or auditory brainstem implants. For example, cochlear implants can provide a person having sensorineural hearing loss with the ability to perceive sound by stimulating the person's auditory nerve via an array of electrodes implanted in the person's cochlea. A component of the cochlear implant detects sound waves, which are converted into a series of electrical stimulation signals that are delivered to the implant recipient's cochlea via the array of electrodes. Auditory brainstem implants can use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound. Further, some persons may benefit from hearing prosthesis that combine one or more characteristics of the acoustic hearing aids, vibration-based hearing devices, cochlear implants, and auditory brainstem implants to enable the person to perceive sound.

The effectiveness of a hearing prosthesis depends generally on the design of the prosthesis itself and on how well the prosthesis is configured for or fitted to a prosthesis recipient. The fitting of the prosthesis, sometimes also referred to as programming or mapping creates a set of configuration settings and other data that define the specific characteristics of the signals (acoustic, mechanical, or electrical) delivered to the relevant portions of the person's outer ear, middle ear, inner ear, or auditory nerve. Generally, it is desirable to improve on the arrangements of the prior art or at least to provide one or more useful alternatives.

SUMMARY

The present application discloses systems, methods, and articles of manufacture for fitting a hearing prosthesis to a prosthesis recipient. In various non-limiting examples, the hearing prosthesis can be a cochlear implant, a bone anchored device, a direct acoustic cochlear stimulation device, an auditory brain stem implant, an acoustic hearing aid, or any other type of hearing prosthesis configured to assist a prosthesis recipient in perceiving sound.

Some embodiments are directed to a method that includes identifying a threshold hearing level and an uncomfortable loudness level for a frequency channel. In one example, the threshold hearing level and the uncomfortable loudness level are determined in response to a stimulation signal generated utilizing the hearing prosthesis in situ on a recipient. In the present example, the stimulation signal corresponds to the frequency channel. The method further includes developing a prescription rule based on the threshold hearing level and the uncomfortable loudness level. Generally, the prescription rule includes at least one of a linear compression scheme and a wide dynamic range compression scheme.

Other embodiments are directed to a system that includes one or more processors configured to cause the hearing prosthesis to generate an output signal that corresponds to an output frequency band, identify a first level at which a recipient of the hearing prosthesis first perceives the output signal, identify a second level at which the recipient finds the output signal to be uncomfortable, and develop a sound input/output gain scheme for the hearing prosthesis and the recipient based on the first and second levels. The gain scheme includes first, second, and third regions that correspond to regions having high, medium, and low input sound levels, respectively.

Still other embodiments are directed to an article of manufacture including computer-readable media with instructions stored thereon. The instructions include instructions for retrieving data related to a hearing prosthesis recipient's dynamic sound perception range and instructions for determining configuration settings from the dynamic sound perception range. The configuration settings define a relationship between an input signal and an output signal that is perceived as sound by the recipient. Further, the relationship may include first, second, and third regions that each include different relationships between the input signal and the output signal.

DETAILED DESCRIPTION

The following detailed description describes various features, functions, and attributes of the disclosed systems, methods, and articles of manufacture with reference to the accompanying figures. In the figures, similar symbols typically identify similar components, unless context dictates otherwise. The illustrative embodiments described herein are not meant to be limiting. Certain aspects of the disclosed systems, methods, and articles of manufacture can be arranged and combined in a wide variety of different configurations, all of which are contemplated herein.

Figure 1:
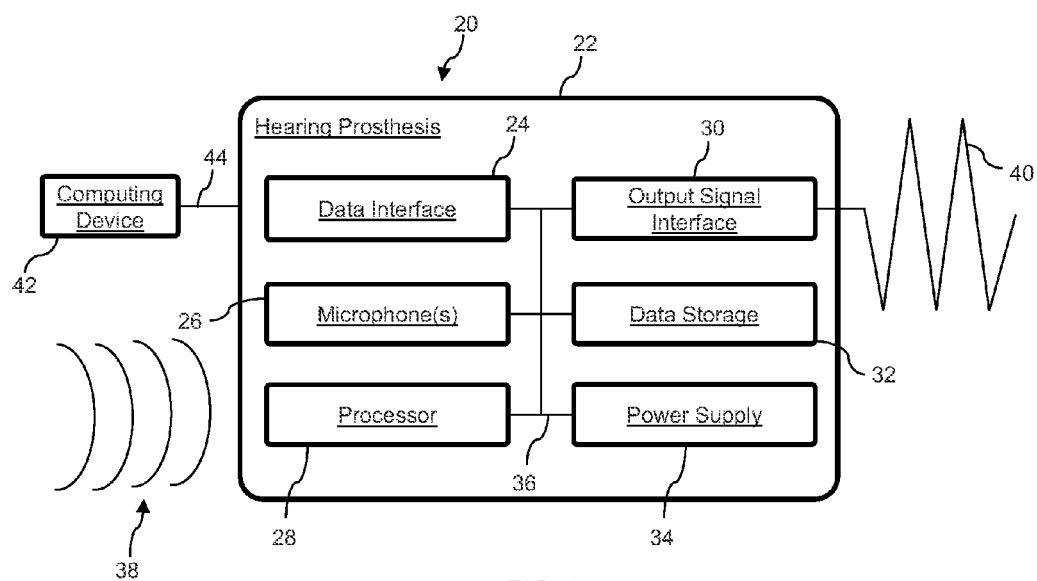
FIG. 1 illustrates a block diagram of a hearing prosthesis system according to an embodiment of the present disclosure.

FIG. 1 shows one example system 20 that includes a hearing prosthesis 22 configured according to some embodiments of the disclosed systems, methods, and articles of manufacture. In various examples, the hearing prosthesis 22 can be a cochlear implant, an acoustic hearing aid, a bone anchored device, a direct acoustic stimulation device, an auditory brain stem implant, or any other type of hearing prosthesis configured to assist a prosthesis recipient in perceiving sound.

The hearing prosthesis 22 illustrated in FIG. 1 includes a data interface 24, one or more microphones 26, one or more processors 28, an output signal interface 30, data storage 32, and a power supply 34 all of which are illustrated as being connected directly or indirectly via a system bus or other known circuitry 36. The one or more microphones 26 generally include combinations of one or more omnidirectional and directional microphones so that the hearing prosthesis 22 can be configured to process background sounds and/or to focus on sounds from a specific direction, such as generally in front of the prosthesis recipient.

Further, the power supply 34 supplies power to various components of the hearing prosthesis 22 and can be any suitable power supply, such as a non-rechargeable or rechargeable battery. In one example, the power supply 34 is a battery that can be recharged wirelessly, such as through inductive charging. Such a wirelessly rechargeable battery would facilitate complete subcutaneous implantation of the hearing prosthesis 22 to provide a fully implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined, or otherwise, associated with use of the prosthesis.

The data storage 32 generally includes any suitable volatile and/or non-volatile storage components. Further, the data storage 32 may include computer-readable program instructions and perhaps additional data. In some embodiments, the data storage 32 stores data and instructions used to perform at least part of the herein-described methods and algorithms and/or at least part of the functionality of the systems described herein.

Various modifications can be made to the hearing prosthesis 22 illustrated in FIG. 1, for example, the prosthesis may include additional or fewer components arranged in any suitable manner. In some examples, the prosthesis 22 may include other components to process external audio signals, such as components that measure vibration in the skull caused by audio signals and/or components that measure electrical output of portions of a person's hearing system in response to audio signals. Further, depending on the type and design of the hearing prosthesis 22, the illustrated components may be enclosed within a single operational unit or distributed across multiple operational units (e.g., two or more internal units or an external unit and an internal unit).

Generally, in use, the microphone(s) 26 are configured to receive external acoustic signals 38 and the processor 28 is configured to analyze and encode the acoustic signals into output signals 40 for application to the implant recipient via the output signal interface 30. The external acoustic signals 38 are generally encoded into output signals 40 in accordance with configuration settings, which include prescription rules, as will be described in more detail hereinafter.

For example, in embodiments where the hearing prosthesis 22 is a direct acoustic cochlear stimulation (DACS) device, the microphone(s) 26 are configured to receive acoustic signals 38 and the processor 28 is configured to analyze and encode the acoustic signals into mechanical vibration output signals 40. The mechanical vibration output signals 40 are applied to the DACS recipient's inner ear via the output signal interface 30 that, in the present example, includes an actuator to transmit sound via direct mechanical stimulation.

Similarly, for embodiments where the hearing prosthesis 22 is a bone anchored device, the microphone(s) 26 and the processor 28 are configured to receive, analyze, and encode acoustic signals 38 into mechanical vibration output signals 40. The mechanical vibration output signals 40 are applied to the bone anchored device recipient's skull via the output signal interface 30 that, in the present example, includes an actuator to transmit sound via direct bone vibrations.

In addition, for embodiments where the hearing prosthesis 22 is an auditory brain stem implant, the microphone(s) 26 and the processor 28 are configured to receive, analyze, and encode the acoustic signals 38 into electrical stimulation output signals 40. The electrical stimulation output signals 40 are applied to the auditory brain stem implant recipient's auditory nerve via the output signal interface 30 that, in the present example, includes one or more electrodes.

Similarly, in embodiments where the hearing prosthesis 22 is a cochlear implant, the microphone(s) 26 and the processor 28 are configured to receive, analyze, and encode the external acoustic signals 38 into electrical stimulation output signals 40. The electrical stimulation output signals 40 are applied to an implant recipient's cochlea via the output signal interface 30, which may include an array of electrodes, for example.

In embodiments where the hearing prosthesis 22 is an acoustic hearing aid or a combination electric and acoustic hybrid hearing prosthesis, the microphone(s) 26 and the processor 28 are configured to receive, analyze, and encode acoustic signals 38 into acoustic output signals 40 that are applied to a recipient's ear via the output signal interface 30 comprising a speaker, for example.

Referring now to the data interface 24, the interface can be utilized to load a recipient's configuration data into the prosthesis 22. The configuration data can then be stored in the data storage 32. A recipient's configuration data allows the hearing prosthesis 22 to be configured for or fitted to a recipient. Generally, the configuration data includes gain prescription rules and other configuration data that defines how the processor 28 of the prosthesis 22 analyzes and converts the acoustic signals 38 received by the microphone(s) 26 to output signals 40 transmitted to the prosthesis recipient via the output signal interface 30.

In one example, a computing device 42 can be used to develop and/or load the recipient's prescription rule to the data interface 24 through a communication connection 44. The communication connection 44 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, and the like.

One generic prescription rule for a hearing prosthesis is based on a decibels hearing level (dB HL) scale that is based on the quietest sounds that an average individual with healthy hearing can hear. The dB HL scale is typically considered a universal scale across humans and can be used to predict a required gain to compensate for hearing loss. However, with some hearing prosthesis, acoustic coupling to a recipient may be variable and use of the dB HL scale may not provide an ideal prescription. In accordance with one example, a fitting application can be executed utilizing the computing device 42 and the hearing prosthesis 22 in place on the recipient to develop a customized prescription. In the present example, the customized prescription is based on the recipient's dynamic hearing range, as will be described in more detail hereinafter.

Further, the recipient or a third party, such as a guardian of a minor recipient or a health care professional, can utilize the computing device 42 to control the hearing prosthesis 22. For example, the computing device 42 may include input devices, such as buttons, dials, a touch screen with a graphic user interface, and the like, that can be used to turn the prosthesis 22 on and off, adjust the volume, switch between one or more operating modes, adjust or fine tune the prescription, etc.

Figure 2:
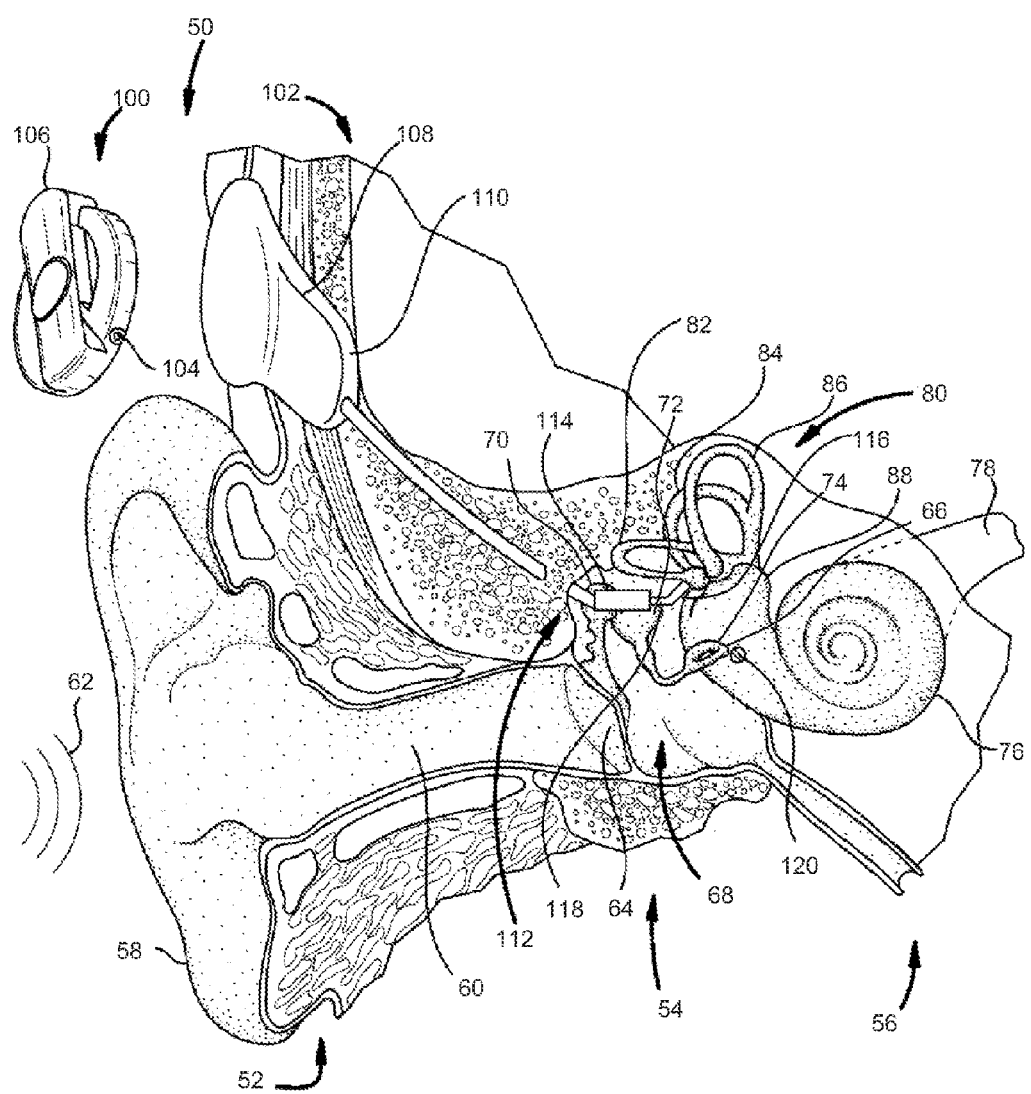
FIG. 2 is a perspective, partially cut-away view of a direct mechanical stimulator in accordance with an embodiment of the present disclosure shown implanted in a recipient.

Referring now to FIG. 2, a DACS device 60 in accordance with an embodiment of the present disclosure is illustrated with components coupled to an individual's hearing system, which generally includes an outer ear 52, a middle ear 54, and an inner ear 56. In a fully functional ear, the outer ear 52 comprises an auricle 58 and an ear canal 60. An acoustic pressure or sound wave 62 is collected by the auricle 58 and channeled into and through the ear canal 60. A tympanic membrane 64 is disposed across a distal end of the ear canal 60. The tympanic membrane 64 vibrates in response to the sound wave 62. Such vibration is transferred to an oval window or fenestra ovalis 66 through three bones of the middle ear 54, collectively referred to as ossicles 68, and comprising a malleus 70, an incus 72, and a stapes 74. The bones 70-74 of the middle ear 54 serve to filter and amplify the sound wave 62 and cause the oval window 66 to articulate or vibrate in response to vibration of the tympanic membrane 64. The oval window 66 is further coupled to a cochlea 76, such that vibration of the oval window sets up waves of fluid motion within the cochlea. Such fluid motion, in turn, activates tiny hair cells (not shown) inside of the cochlea 76. Activation of the hair cells causes appropriate nerve impulses to be generated and transferred through spiral ganglion cells (not shown) and an auditory nerve 78 to the brain (not shown) where they are perceived as sound.

FIG. 2 further illustrates semicircular canals 80, which include three half-circular, interconnected tubes located adjacent the cochlea 76. The three canals include a horizontal semicircular canal 82, a posterior semicircular canal 84, and a superior semicircular canal 86. The canals 82-86 are filled with a fluid and include tiny hairs (not shown). As the recipient's head twists in any direction, the fluid is forced into different sections of the canals 82-86. The hairs within the canals 82-86 detect when the fluid passes thereby and a signal is sent to the brain. Using the hair cells within the canals 82-86, the horizontal canal detects horizontal head movements, while the superior and posterior canals detect vertical head movements. A vestibule 88 provides fluid communication between the fluid in the canals 82-86 and the fluid in the cochlea 76.

Referring again to the DACS device 50, the illustrated device includes an external component 100 that is directly or indirectly attached to the body of the recipient and an internal component 102 that is temporarily or permanently implanted in the recipient. The external component 100 typically comprises one or more sound input elements, such as microphones 104 for detecting sound, a sound processing unit 106, a power source (not shown), and an external transmitter unit (also not shown). The external transmitter unit is disposed on an exterior surface of the sound processing unit 106 and comprises an external coil (not shown). The sound processing unit 106 processes the output of the microphones 104 and generates encoded data signals, which are provided to the external transmitter unit. For ease of illustration, the sound processing unit 106 is shown detached from the recipient.

The internal component 102 includes an internal receiver unit 108, a stimulator unit 110, and a stimulation arrangement 112. The internal receiver unit 108 and the stimulator unit 110 can be hermetically sealed within a biocompatible housing. In one example, the internal receiver unit 108 includes an internal coil (not shown) and a magnet (not shown) fixed relative to the internal coil. The external coil transmits electrical signals, such as power and stimulation data, to the internal coil via a radio frequency (RF) link, for example. The internal coil can be a wire antenna coil comprised of multiple turns of electrically insulated single-strand or multi-strand wire, such as platinum or gold wire. Generally, in use, the internal receiver unit 108 may be positioned in a recess of the temporal bone adjacent an auricle 58 of the recipient.

In the illustrative embodiment, the stimulation arrangement 112 is implanted in the middle ear portion 54 of the recipient. In the present example, the stimulation arrangement 112 includes an actuator 114, a stapes prosthesis 116, and a coupling element 118.

The stimulation arrangement 112 can be implanted and/or configured such that a portion of the stapes prosthesis 116 abuts an opening in one of the semicircular canals 80 of the recipient. By way of non-limiting example, the stapes prosthesis 116 can be configured to abut an opening in the horizontal semicircular canal 82 of the recipient. It would be appreciated that in other examples, the stimulation arrangement 112 may be implanted such that the stapes prosthesis 116 abuts an opening in the posterior semicircular canal 84 or the superior semicircular canal 86 of the recipient. In still other examples, the stapes prosthesis 116 can be configured to abut a round window 120 or other portions of the recipient's cochlea 76.

Generally, in use, a sound signal is received by the one or more microphones 104, processed by the sound processing unit 106, and transmitted as encoded data signals to the internal receiver unit 108. Based on these received signals, the stimulator 110 is configured to generate drive signals that cause actuation of the actuator 114. Such actuation is transferred to the stapes prosthesis 116 such that a wave of fluid motion is generated in the horizontal semicircular canal 80. The vestibule 88 provides fluid communication between the semicircular canals 80 and the cochlea 76 so that the wave of fluid motion continues in the cochlea thereby activating hair cells therein. Activation of the hair cells causes appropriate nerve impulses to be generated and transferred through the spiral ganglion cells and the auditory nerve 78 to the brain where the impulses are perceived by the recipient as sound.

Figure 3:
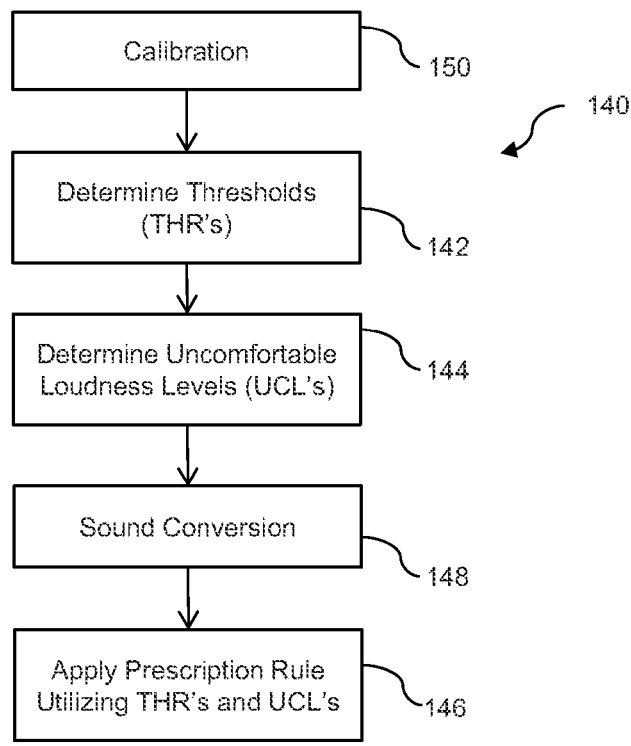
FIG. 3 is a flowchart showing a method or algorithm for determining prescription rules for a hearing prosthesis according to an embodiment.

Referring now more particularly to FIG. 3 and with further reference to FIGS. 1 and 2, one example method 140 is illustrated for determining prescriptions rules for a hearing prosthesis and a recipient according to an embodiment. For illustration purposes, some features and functions are described herein with respect to direct acoustic cochlear stimulation devices. However, many features and functions may be equally applicable to other types of hearing prostheses.

The method 140 of FIG. 3 begins at blocks 142, 144 during which threshold hearing levels (THRs) and uncomfortable loudness levels (UCLs) of a hearing prosthesis are determined for different sound frequencies. More particularly, the blocks 142, 144 generate noise stimuli signals, such as clicks, tones, speech, etc. that are applied to the recipient through the output signal interface 30. In one example, the hearing prosthesis is the DACS device 50 of FIG. 2 and the tones are applied through the actuator 114 by direct mechanical stimulation. The tones may include single frequency pure tones or tones across a frequency band. In one example, the tones are pure tones generated as pulses of a continuous tone or a plurality of discrete tones. The pulses have various variable parameters, such as frequency and amplitude of the tone, duration of a pulse, time between pulses, number of discrete tones in a pulse, fade in and fade out durations, number of times a pulse at a given frequency and/or amplitude is repeated, etc.

In the present example, pure tones at a given frequency are generated in pulses with gradually increasing amplitudes as the recipient identifies how the tone is perceived. More particularly, the recipient identifies when they first perceive the tone, which corresponds to the THR, and when the tone loudness becomes uncomfortable, which corresponds to the UCL. Once the THR and UCL are determined for a given frequency, a tone with a different frequency can be applied and the process repeated to obtain THR and UCL data for different frequencies throughout a normal hearing range of a recipient. In one example, the THRs and UCLs are determined for a plurality of frequencies including 250 Hz, 500 Hz, 1 kHz, 1500 Hz, 2 kHz, and 4 kHz, plus or minus about 10%. In other examples, additional or fewer frequencies can be utilized up to and beyond about 8000 Hz.

The THR and the UCL data can then be used to define a dynamic sound range that the recipient is able to perceive utilizing the hearing prosthesis in situ. More particularly, following the blocks 142, 144, control passes to a block 146 and the THR and the UCL are used to define a prescription rule for the hearing prosthesis and the recipient. Generally, the prescription rule defines a relationship between an input level and an output level for a given channel or frequency band, which can represent a single frequency or a plurality of continuous or discontinuous frequencies.

The method 140 illustrated in FIG. 3 also includes an optional sound conversion block 148. In one example, the hearing prosthesis is a DACS device and each THR and UCL data point determined during the blocks 142, 144 is converted during the block 148 to an equivalent decibel sound pressure level (dB $SPL_{eq}$) and an equivalent decibel hearing level (dB $HL_{eq}$). The dB $SPL_{eq}$ and dB $HL_{eq}$ can be used to determine configuration settings, including prescription rules for a hearing prosthesis. In the present example, a vibration of the actuator of the DACS device, which is typically measured in mm/s, is converted to an equivalent sound pressure level within the ear of the recipient using a conversion table. In one example, the following Equation (1) is utilized to perform the sound conversion of the block 148:

$$dB\ HL_{eq} = dB\ SPL_{eq} - RECD - RETSPL \quad (1)$$

In Equation (1), RECD is a "real ear to coupler difference" value and RETSPL is a "reference equivalent threshold sound pressure level" value, which can be determined from the following conversion Table 1:

TABLE 1

Nominal values for all transformations: A, free field to eardrum; B, free field to BTE mic location: C, free field to ITE mic location; D, free field to ITC mic location; E, 6 cc to eardrum; F, 2 cc to eardrum; G, 2 cc to free field; H, HL to SPL (2 cc); I, CORFIG BTE; J, CORFIG ITE; K, CORFIG ITC; L, MAF; M, MAP; N, MAPC.

| Frequency | A | B | C | D | E | F | G | H | I | J | K | L | M | N |
|---|---|---|---|---|---|---|---|---|---|---|---|---|---|---|
| Third Octave Center | | | | | | | | | | | | | | |
| 160 | NA | 0.0 | NA | NA | NA | NA | NA | NA | NA | NA | NA | NA | NA | NA |
| 200 | 0.5 | 0.5 | 0.3 | 0.0 | -13.9 | 4.0 | 3.5 | 14.6 | -4.0 | -3.8 | -3.5 | 15.3 | 15.8 | 32.5 |
| 250 | 1.0 | 0.5 | 0.5 | 0.3 | -9.8 | 4.0 | 3.0 | 12.2 | -3.5 | -3.5 | -3.3 | 12.7 | 13.7 | 26.0 |
| 315 | 1.4 | 0.8 | 0.8 | 0.3 | -7.0 | 4.0 | 2.6 | 10.5 | -3.4 | -3.4 | -2.9 | 10.5 | 11.9 | 21.5 |
| 400 | 1.5 | 1.1 | 1.0 | 0.7 | -3.2 | 4.0 | 2.5 | 9.6 | -3.6 | -3.5 | -3.2 | 8.7 | 10.2 | 16.8 |
| 500 | 1.8 | 1.2 | 1.8 | 0.0 | -0.8 | 4.2 | 2.4 | 7.5 | -3.6 | -4.2 | -2.4 | 7.5 | 9.3 | 12.5 |
| 630 | 2.4 | 1.1 | 2.0 | 0.1 | 0.6 | 4.3 | 1.9 | 6.4 | -3.0 | -3.9 | -2.0 | 6.5 | 8.9 | 10.1 |
| 800 | 3.1 | 0.9 | 2.0 | 0.4 | 1.9 | 4.5 | 1.4 | 5.4 | -2.3 | -3.4 | -1.8 | 5.9 | 9.0 | 8.0 |
| 1000 | 2.6 | 0.3 | 1.5 | 1.2 | 2.2 | 5.2 | 2.6 | 4.3 | -2.9 | -4.1 | -3.8 | 5.7 | 8.3 | 7.3 |
| 1250 | 3.0 | 0.6 | 0.3 | -1.6 | 2.1 | 6.1 | 3.1 | 3.1 | -3.7 | -3.4 | -1.5 | 5.3 | 8.3 | 7.1 |
| 1600 | 6.1 | 2.5 | -0.3 | -1.9 | 3.5 | 6.6 | 0.5 | 4.6 | -3.0 | -0.2 | 1.4 | 4.1 | 10.2 | 7.7 |
| 2000 | 12.0 | 4.1 | 3.8 | 2.1 | 5.9 | 8.0 | -4.0 | 7.9 | -0.1 | -0.2 | 1.9 | 2.5 | 14.5 | 10.0 |
| 2500 | 16.8 | 3.5 | 5.0 | 4.8 | 7.9 | 9.3 | -7.5 | 8.4 | 4.0 | 2.5 | 2.7 | 0.3 | 17.1 | 9.8 |
| 3150 | 15.0 | 2.8 | 3.3 | 3.5 | 5.3 | 10.5 | -4.5 | 4.6 | 1.7 | 1.2 | 1.0 | -1.6 | 13.4 | 9.8 |
| 4000 | 14.3 | 3.7 | 4.3 | 6.4 | 3.4 | 12.2 | -2.1 | 1.2 | -1.6 | -2.2 | -4.3 | -1.9 | 12.4 | 10.0 |
| 5000 | 10.7 | -1.2 | 4.3 | 6.6 | 0.4 | 13.6 | 2.9 | -0.7 | -1.7 | -7.2 | -9.5 | 1.4 | 12.3 | 12.5 |
| 6300 | 6.4 | 1.6 | -0.4 | -1.8 | 2.7 | 14.7 | 8.4 | 2.2 | -9.9 | -7.9 | -6.5 | 10.4 | 16.8 | 14.2 |
| 8000 | 1.8 | 3.3 | 1.0 | -1.9 | NA | 15.0 | 13.2 | NA | -16.5 | -14.2 | -11.3 | 20.6 | 22.4 | 13.0 |

More particularly, in one example, the values in column F correspond to the RECD values at different frequencies and the values in column H correspond to the RETSPL values at different frequencies. Additional values for RECD and RETSPL for frequencies not listed in Table 1 can be calculated by any appropriate method, such as logarithmic interpolation. In other examples, such as with a cochlear implant, the electrical output signals of the implant can be converted to dB $SPL_{eq}$ and/or dB $HL_{eq}$ levels for use with systems and methods disclosed herein.

Further, the method 140 illustrated FIG. 3 includes an optional calibration block 150 to ensure that an output of a hearing prosthesis is accurately known. More particularly, the calibration block 150 in accordance with one example determines an input calibration, which calibrates one or more microphones, and an output calibration, which calibrates an output signal interface. Generally, the input calibration can be performed using a speaker system with known audio output levels and measuring audio input levels received by the microphones. Further, the output calibration can be performed by measuring a maximum output of the output signal interface, such as the actuator 114 of a DACS device, and attenuating the maximum output to shift a dynamic range of the output signal interface to an appropriate range for the hearing prosthesis in use. The calibration of the block 150 may be performed for each hearing prosthesis during production and the calibration results stored in a processor thereof. Alternatively, average calibration results can be calculated and applied to multiple hearing prostheses.

Various modifications can be made to the example of FIG. 3. For example, the blocks 142, 144 can be combined into a single block. Other modifications, such as having additional or fewer blocks and/or rearranging the order of the blocks, are also contemplated.

Figure 4:
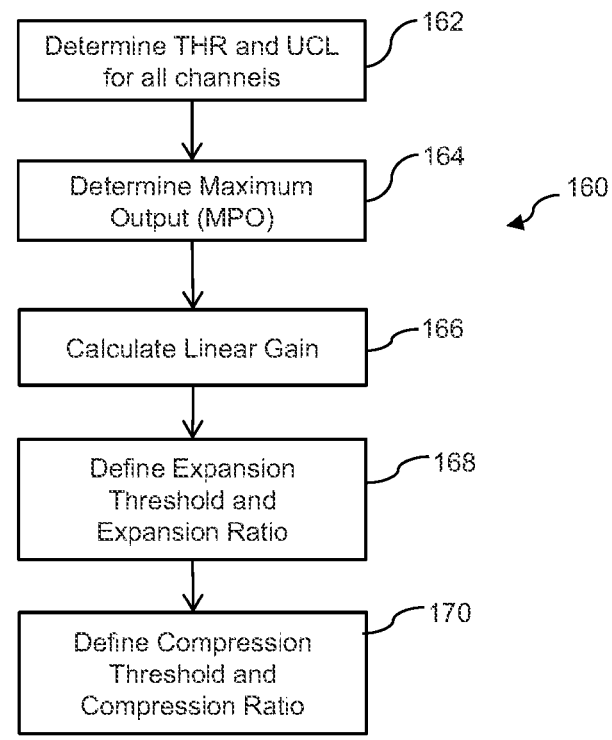
FIG. 4 is another flowchart showing a method or algorithm for determining prescription rules for a hearing prosthesis according to an embodiment.
Figure 5:
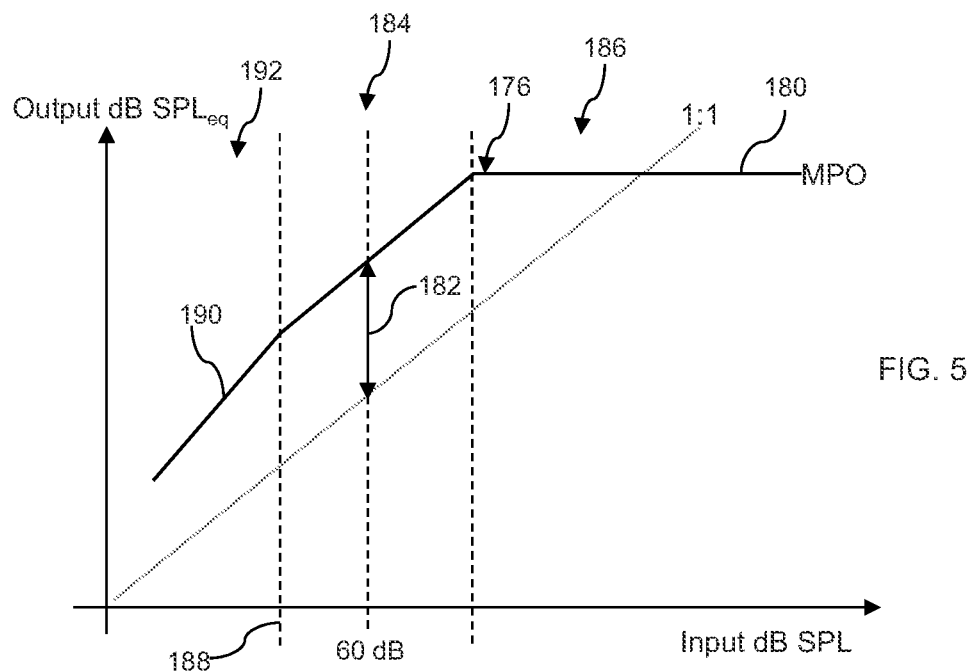
FIG. 5 is a graph showing a linear compression prescription rule.
Figure 6:
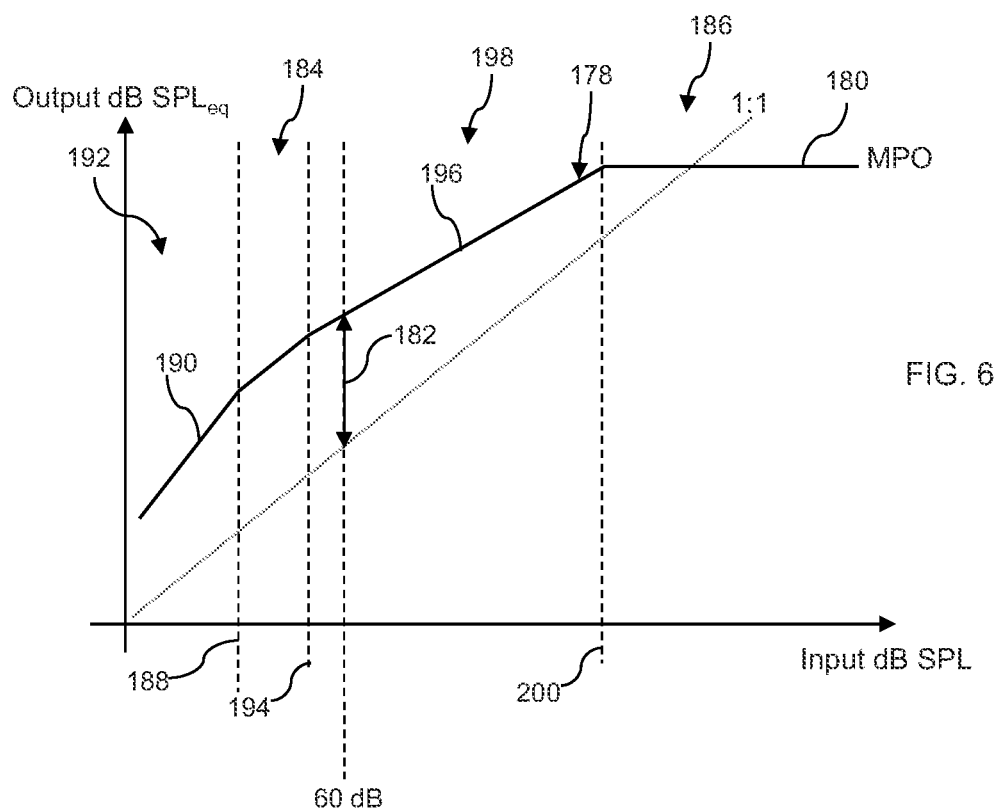
FIG. 6 is a graph showing a wide dynamic range compression prescription rule.

Referring now to FIG. 4, an example method 160 is illustrated for determining a prescription rule for the hearing prosthesis and the recipient. Generally, the prescription rule defines a relationship between an input level and an output level for a given channel. The prescription rule may include, for example, a linear compression scheme (as illustrated generally by line 176 in FIG. 5) and/or a wide dynamic range compression (WDRC) scheme (as illustrated generally by line 178 in FIG. 6). In FIGS. 5 and 6, a horizontal axis corresponds to an input dB SPL and a vertical axis corresponds to an output dB $SPL_{eq}$. As described generally above, dB $SPL_{eq}$ can be used to represent equivalent sound output levels generated by the hearing prosthesis. The present disclosure contemplates modifications to the FIGS. 5 and 6, in which other representations of input and output levels of a hearing prosthesis can be used.

In one example, the hearing prosthesis is a DACS device and, in use, the linear compression scheme 176 may be desirable if the THR values are less than or equal to about 75 dB HL for 500 Hz and 1 kHz, otherwise, the WDRC scheme 178 may be desirable.

Referring more particularly to the linear compression scheme 176 of FIG. 5, the method 160 of FIG. 4 begins at a block 162 to determine the THRs and UCLs for all relevant channels or frequencies. Generally, the channels define frequency bands that divide a normal hearing range of a recipient. In one example, the channels define up to about 20 frequency bands between about 60 Hz and 9000 Hz.

Next, control passes to a block 164 to determine a maximum output (MPO) 180 based on the measured UCL for each channel. In one example, the following Equation (2) is used to calculate the MPO 180:

$$MPO = UCL - X \qquad (2).$$

In Equation (2), X is a correction value used to compensate for a summation effect in case a loud sound is present in multiple channels simultaneously and can be a value between about 3 dB and 12 dB. In one example, X is 6 dB. Next, control passes to a block 166 and a linear gain 182 is calculated using the following Equation (3):

$$GAIN = [(UCL + THR) * 0.5] - 60 \text{ dB} \qquad (3).$$

In one example, the linear gain 182 is the gain applied at about 60 dB SPL, which approximates the most comfortable listening level for normal hearing. However, the 60 dB normal listening level can be modified in other examples of the present disclosure. Further, the linear gain 182 represents a linear region 184 of the prescription rule where the input level and the output level have a 1:1 ratio. The linear gain 182 increases in the linear region 184 until it reaches the MPO 180, at which point an output-limiting region 186 begins where the output level is capped to the MPO.

In other examples, the linear gain 182 can include a frequency correction and/or a microphone location effect (MLE) correction. The frequency correction can be made to achieve an appropriate balance between high and low frequency components of amplified speech. As a general rule, the frequency correction can be utilized to improve speech understanding by ensuring that low frequency outputs of a hearing prosthesis are less than or equal to high frequency outputs. In one example, the frequency correction utilizes a modified form of Equation (3), i.e., the following Equation (4):

$$GAIN = [(UCL + THR) * 0.5] - 60 \text{ dB} + FreqCorr \qquad (4)$$

In one example, FreqCorr is determined by the following Table (2):

| | Frequency | | | | | | | | |
|---|---|---|---|---|---|---|---|---|---|
| | 250 | 500 | 750 | 1000 | 1500 | 2000 | 3000 | 4000 | 6000 |
| FreqCorr | −3.5 | −3.4 | −0.1 | 3.6 | 7.0 | 9.6 | 15.1 | 16.6 | 11.6 |

However, the frequency correction can be modified in other examples depending on the intended use of the prescription rule, such as to assist the recipient to perceive music.

Further, in one example, the MLE correction can be used to account for the influence of microphone location on how a hearing prosthesis receives an external acoustic signal. In the present example, the MLE correction utilizes a modified form of Equations (3) or (4), in particular, by subtracting the MLE value as provided in Equation (5):

$$GAIN = [(UCL + THR) * 0.5] - 60 \text{ dB} + FreqCorr - MLE \qquad (5)$$

In one example, MLE can be determined by the following Table (3):

TABLE 3

Nominal values for all transformations: A, free field to eardrum; B. free field to BTE min location: C. tree field to ITE mic location; D. free field to ITC mic location; E. 6 cc to eardrum: F. 2 cc to eardrum: G. 2 cc to free field; H, HL to SPL (2 cc); I, CORFIG BTE; J, CORFIG ITE: K, CORFIG ITC; L, MAF; M, MAP: N. MAPC.

| Frequency | A | B | C | D | E | F | G | H | I | J | K | L | M | N |
|---|---|---|---|---|---|---|---|---|---|---|---|---|---|---|
| Third Octave Center | | | | | | | | | | | | | | |
| 160 | NA | 0.0 | NA | NA | NA | NA | NA | NA | NA | NA | NA | NA | NA | NA |
| 200 | 0.5 | 0.5 | 0.3 | 0.0 | −13.9 | 4.0 | 3.5 | 14.6 | −4.0 | −3.8 | −3.5 | 15.3 | 15.8 | 32.5 |
| 250 | 1.0 | 0.5 | 0.5 | 0.3 | −9.8 | 4.0 | 3.0 | 12.2 | −3.5 | −3.5 | −3.3 | 12.7 | 13.7 | 26.0 |
| 315 | 1.4 | 0.8 | 0.8 | 0.3 | −7.0 | 4.0 | 2.6 | 10.5 | −3.4 | −3.4 | −2.9 | 10.5 | 11.9 | 21.5 |
| 400 | 1.5 | 1.1 | 1.0 | 0.7 | −3.2 | 4.0 | 2.5 | 9.6 | −3.6 | −3.5 | −3.2 | 8.7 | 10.2 | 16.8 |
| 500 | 1.8 | 1.2 | 1.8 | 0.0 | −0.8 | 4.2 | 2.4 | 7.5 | −3.6 | −4.2 | −2.4 | 7.5 | 9.3 | 12.5 |
| 630 | 2.4 | 1.1 | 2.0 | 0.1 | 0.6 | 4.3 | 1.9 | 6.4 | −3.0 | −3.9 | −2.0 | 6.5 | 8.9 | 10.1 |
| 800 | 3.1 | 0.9 | 2.0 | 0.4 | 1.9 | 4.5 | 1.4 | 5.4 | −2.3 | −3.4 | −1.8 | 5.9 | 9.0 | 6.0 |
| 1000 | 2.6 | 0.3 | 1.5 | 1.2 | 2.2 | 5.2 | 2.6 | 4.3 | −2.9 | −4.1 | −3.8 | 6.7 | 8.3 | 7.3 |
| 1250 | 3.0 | 0.6 | 0.3 | −1.6 | 2.1 | 6.1 | 3.1 | 3.1 | −3.7 | −3.4 | −1.5 | 5.3 | 8.3 | 7.1 |
| 1600 | 6.1 | 2.5 | −0.3 | −1.9 | 3.5 | 6.6 | 0.5 | 4.6 | −3.0 | −0.2 | 1.4 | 4.1 | 10.2 | 7.7 |
| 2000 | 12.0 | 4.1 | 3.8 | 2.1 | 5.9 | 8.0 | −4.0 | 7.9 | −0.1 | −0.2 | 1.9 | 2.5 | 14.5 | 10.0 |
| 2500 | 16.8 | 3.5 | 5.0 | 4.8 | 7.9 | 9.3 | −7.5 | 8.4 | 4.0 | 2.5 | 2.7 | 0.3 | 17.1 | 9.8 |
| 3150 | 15.0 | 2.8 | 3.3 | 3.5 | 5.3 | 10.5 | −4.5 | 4.6 | 1.7 | 1.2 | 1.0 | −1.6 | 13.4 | 9.8 |
| 4000 | 14.3 | 3.7 | 4.3 | 6.4 | 3.4 | 12.2 | −2.1 | 1.2 | −1.6 | −2.2 | −4.3 | −1.9 | 12.4 | 10.0 |
| 5000 | 10.7 | −1.2 | 4.3 | 6.6 | 0.4 | 13.6 | 2.9 | −0.7 | −1.7 | −7.2 | −9.5 | 1.4 | 12.3 | 12.5 |
| 6300 | 6.4 | 1.6 | −0.4 | −1.8 | 2.7 | 14.7 | 8.4 | 2.2 | −9.9 | −7.9 | −6.5 | 10.4 | 16.8 | 14.2 |
| 8000 | 1.8 | 3.3 | 1.0 | −1.9 | NA | 15.0 | 13.2 | NA | −16.5 | −14.2 | −11.3 | 20.6 | 22.4 | 13.0 |

Referring to FIG. 4, the method 160 further includes a block 168 to determine an expansion threshold (ET) 188 and an expansion ratio (ER) 190. In the present example, the ER, defines the gain in an expansion region 192 of the prescription rule where the ratio between the input level and the output level is less than one. The expansion region 192 is generally used to reduce low-level system noise and the ER 190 can be any appropriate value to accomplish such reduction. Further, the ER 190 can be channel dependent, for example, the ER can equal 0.66 for a lower frequency band and 0.5 for a higher frequency band. The ET 188 defines where the expansion region 192 ends and the linear region begins 184. In one example, the ET 188 is set to a default setting of about 35 dB and the ER 190 is set to a default setting of about 0.7. However, in the present example, the ET 188 and the ER 190 can be modified from the default settings.

Referring now more particularly to the WDRC scheme 178 of FIG. 6, the algorithm of FIG. 4 further includes a block 170, which can be performed to obtain the WDRC prescription rule, which is similar to the linear prescription rule of FIG. 5. More particularly, the block 170 determines a compression threshold (CT) 194 and a compression ratio (CR) 196. In the present example, the CR 196 defines the gain in a compression region 198 of the prescription rule where the ratio between the input level and the output level is greater than one. The compression region 198 is generally used to avoid over amplifying loud sounds and the CR 196 can be any appropriate value to avoid such over amplifying. Further, the CR 196 can differ between different channels. The CT 194 defines where the linear region 184 ends and the compression region 198 begins. In one example, the CT 194 is set to a default setting of about 50 dB SPL. Further, the CR 196 is determined by the linear gain 182 at 60 dB and the MPO 180 at an upper input level threshold 200. In one example, the input level 200 is determined by the microphone input at full scale minus 5 dB and is set at a default maximum of 85 dB. Generally, the CR 196 is between about 1.0 and 6.0. However, in the present examples, the CT 194 and the input level 200 can be modified from the default settings.

Various modifications may be made to the illustrative example of FIGS. 4-6. For example, the method may include a fine-tuning block where the compression and gain for soft and/or loud sounds can be automatically and/or manually adjusted. In addition, the prescription rules for different channels may be further fine-tuned with respect to one another to ensure that maximum outputs do not differ beyond a preferred range. Other aspects of the prescription rules may also be adjusted and fine-tuned, such as modifying values of the MPO, ET, ER, CT, CR, etc.

Figure 7:
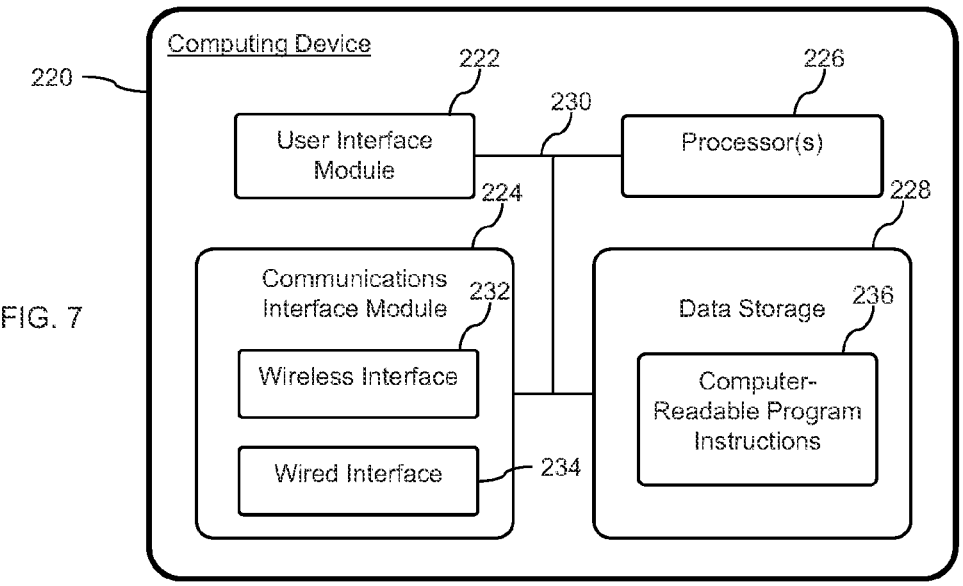
FIG. 7 illustrates a block diagram of a computing device according to an embodiment that can be used to implement certain aspects of the disclosed systems, methods, and articles of manufacture.

Referring now to FIG. 7, a computing device 220 is illustrated, which may be the same or different from the computing device 42 of FIG. 1. Generally, the computing devices 42, 220 can be used to implement certain aspects of some embodiments of the disclosed systems, methods, and articles of manufacture. For example, the computing device 42, 220 can be used as a fitting device that generates noise stimuli and serves as an input device so that the recipient can identify THRs and UCLs.

In FIG. 7, the computing device 220 includes a user interface module 222, a communications interface module 224, one or more processors 226, and data storage 228, all of which are linked together via a system bus or other connection mechanism 230. The user interface module 222 is configured to send data to and/or receive data from user input/output devices such as a keyboard, a keypad, a touch screen, a computer mouse, a track ball, a joystick, and/or other similar devices, now known or later developed. Additionally, the user interface module 222 is also configured to provide outputs to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 222 may also be configured to generate audible output(s), such as a speaker, speaker jack, audio output port, audio output device, earphones, and/or other similar devices, now known or later developed.

In some embodiments, the user interface module 222 also includes (or is communicatively coupled to) an LCD or similar type of touch screen configured to display a user interface. The touch screen may also be configured to receive indications of how a recipient perceives a tone or signal, as described generally above with respect to FIG. 3.

The communications interface module 224 includes one or more wireless interfaces 232 and/or wired interfaces 234 configured to send and receive data to/from a hearing prosthesis via a communications link, such as the connection 44 of FIG. 1. The wireless interfaces 232 may include one or more wireless transceivers, such as a Bluetooth transceiver, a Wi-Fi transceiver, a WiMAX transceiver, and/or other similar type of wireless transceiver configurable to communicate via a wireless protocol. The wired interfaces 234 may include one or more wired transceivers, such as an Ethernet transceiver, a Universal Serial Bus (USB) transceiver, or similar transceiver configurable to communicate via a twisted pair wire, a coaxial cable, a fiber-optic link, or a similar physical connection.

The one or more processors 226 may include one or more general purpose processors (e.g., microprocessors manufactured by Intel, Apple, Advanced Micro Devices, etc.) and/or one or more special purpose processors (e.g., digital signal processors, application specific integrated circuits, etc.). The one or more processors 226 are configured to execute computer readable program instructions 236 stored in the data storage 228 and/or other instructions based on prosthesis fitting algorithms, such as instructions to perform certain aspects of the methods and algorithms described herein with respect to FIGS. 3-4.

The data storage 228 includes one or more computer readable storage media that can be read or accessed by at least one of the processors 226. The one or more computer-readable storage media includes volatile and/or non-volatile storage components, such as optical, magnetic, organic, or other memory or disc storage, which can be integrated in whole or in part with at least one of the processors 226. In some embodiments, the data storage 228 is implemented using a single physical device (e.g., one optical, magnetic, organic or other memory or disc storage unit), while in other embodiments, the data storage is implemented using two or more physical devices. In the present example, the data storage 228 includes the computer readable program instructions 236 and perhaps additional data. In some embodiments, the data storage 228 includes storage required to perform at least some aspects of the methods and algorithms described herein with respect to FIGS. 3-4.

In some embodiments, the disclosed features and functions of the systems, methods, and algorithms shown and described herein may be implemented as computer program instructions encoded on computer-readable media in a machine-readable format.

Figure 8:
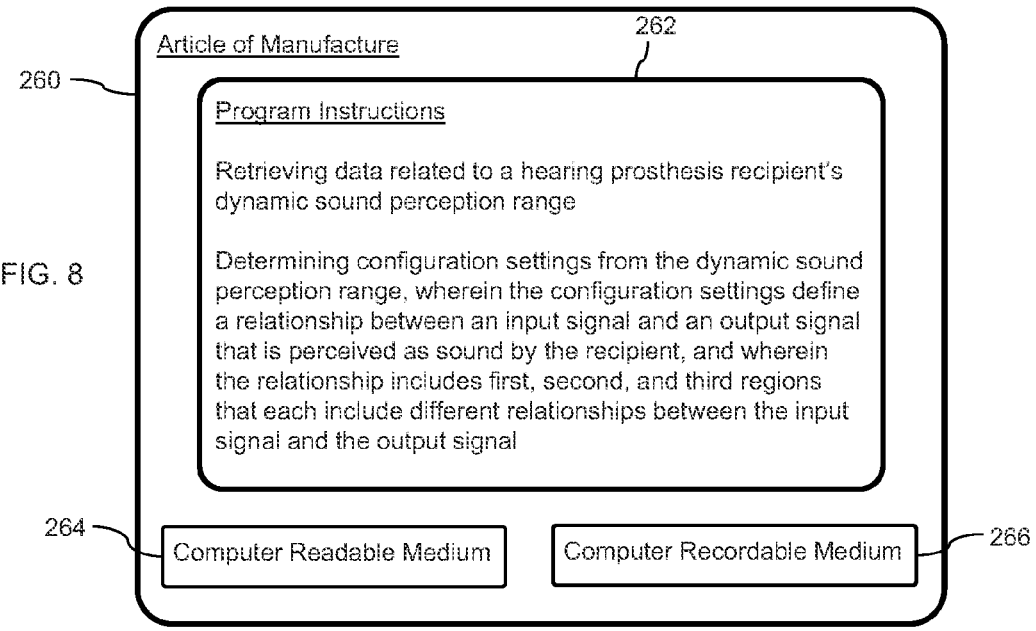
FIG. 8 is a block diagram of an article of manufacture including computer-readable media with instructions for determining prescription rules for a hearing prosthesis according to an embodiment.

FIG. 8 shows an example of an article of manufacture 260 including computer readable media with instructions 262 for determining prescription rules for a hearing prosthesis. In FIG. 8, the example article of manufacture 260 includes computer program instructions 262 for executing a computer process on a computing device, arranged according to at least some embodiments described herein.

In some examples, the article of manufacture 260 includes a computer-readable medium 264, such as, but not limited to, a hard disk drive, a Compact Disc (CD), a Digital Video Disk (DVD), a digital tape, flash memory, etc. In some implementations, the article of manufacture 260 includes a computer recordable medium 266, such as, but not limited to, a hard disk drive, a Compact Disc (CD), a Digital Video Disk (DVD), a digital tape, flash memory, etc.

The one or more programming instructions 262 include, for example, computer executable and/or logic implemented instructions. In some embodiments, a computing device such as the processor 28, the computing device 42, and/or the computing device 220, alone or in combination with one or more additional processors or computing devices, may be configured to perform certain operations, functions, or actions to implement the features and functionality of the disclosed systems and methods based at least in part on the programming instructions 262.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
    identifying a threshold hearing level and an uncomfortable loudness level for a channel of a hearing prosthesis, the threshold hearing level and the uncomfortable loudness level having been identified in response to a stimulation signal generated utilizing the hearing prosthesis, wherein the stimulation signal corresponds to the channel of the hearing prosthesis;
    developing, using a computing device, a prescription rule based on the threshold hearing level and the uncomfortable loudness level, wherein the prescription rule includes at least one of a linear compression scheme or a wide dynamic range compression scheme, wherein each of the linear compression scheme and the wide dynamic range compression scheme includes an expansion threshold and an expansion ratio, wherein the expansion threshold defines where an expansion region of the prescription rule ends and a linear region of the prescription rule begins, wherein the expansion ratio defines a gain in the expansion region where a ratio between an input sound level and a perceived output sound level of the hearing prosthesis is less than 1:1, and wherein a linear gain value of the linear region is determined by averaging the threshold hearing level and the uncomfortable loudness level and subtracting a normal speaking sound level from the average; and
    providing the prescription rule for use by the hearing prosthesis, wherein the hearing prosthesis is configured to utilize the prescription rule to convert an acoustic signal into an output signal that is delivered through the hearing prosthesis to be perceived as sound by a recipient of the hearing prosthesis.

2. The method of claim 1, wherein developing the prescription rule further includes determining a maximum output by subtracting a correction value from the uncomfortable loudness level, wherein the correction value is between 3 dB and 12 dB.

3. The method of claim 1, wherein the linear gain value defines a gain in a linear region of the prescription rule, and wherein a ratio between an input sound level and a perceived output sound level of the hearing prosthesis in the linear region is substantially 1:1.

4. The method of claim 1, further comprising setting the normal speaking sound level to a default of 60 dB.

5. The method of claim 1, wherein developing the prescription rule further includes correcting the linear gain value so that channels that correspond to lower frequencies generally have a lower linear gain value than channels that correspond to higher frequencies.

6. The method of claim 1, wherein developing the prescription rule further includes correcting the linear gain value by subtracting a microphone location effect value.

7. The method of claim 1, further comprising setting the expansion threshold to a default value of 35 dB and the expansion ratio to a default of 0.7:1.

8. The method of claim 1, wherein the prescription rule includes the wide dynamic range compression scheme, wherein developing the prescription rule including the wide dynamic range compression scheme further includes determining a compression threshold and a compression ratio, wherein the compression threshold defines where the linear region of the prescription rule ends and a compression region of the prescription rule begins, and wherein the compression ratio defines a gain in the compression region where a ratio between an input sound level and a perceived output sound level of the hearing prosthesis is greater than 1:1.

9. The method of claim 8, further comprising setting the compression threshold to a default value of 50 dB and determining the compression threshold utilizing the linear gain value at the normal speaking sound level and a maximum output level at an upper input level threshold.

10. The method of claim 9, further comprising determining the maximum output level by subtracting a correction value from the uncomfortable loudness level, wherein the correction value is between 3 dB and 12 dB, and setting the upper input level threshold to a default maximum value of 85 dB.

11. A system, comprising:
one or more processors configured to:
(i) cause the hearing prosthesis to generate an output signal that corresponds to an output frequency band;
(ii) identify a first level at which a recipient of the hearing prosthesis first perceives the output signal;
(iii) identify a second level at which the recipient finds the output signal to be uncomfortable;
(iv) develop a sound input/output gain scheme for the hearing prosthesis and the recipient based on the first and second levels, wherein the gain scheme includes first, second, and third regions that correspond to regions having high, medium, and low input sound levels, respectively, wherein the second region is defined by a gain value calculated by averaging the first and second levels and subtracting a normal speaking sound level from the average, further wherein the second region is defined by a ratio between an input level and an output level that is substantially 1:1; and
(v) provide the gain scheme for use by the hearing prosthesis, wherein the hearing prosthesis is configured to utilize the gain scheme to convert an audio input into an output signal that is delivered through the hearing prosthesis to be perceived as sound by a recipient of the hearing prosthesis.

12. The system of claim 11, wherein the first region is limited to an output defined by the second level minus a correction value between 3 dB and 12 dB.

13. The system of claim 11, wherein the third region is defined by a ratio between an input level and an output level that is less than 1:1.

14. The system of claim 11, further comprising a fourth region of the gain scheme between the first and second regions, and wherein the fourth region is defined by a ratio between an input level and an output level that is greater than 1:1.

15. The system of claim 11, further comprising one or more microphones for receiving the audio input and a stimulation arrangement configured to apply the output signal to a portion of the recipient's hearing system by mechanical stimulation, wherein the mechanical stimulation is perceived by the recipient as sound.

16. An article of manufacture including non-transitory, tangible computer-readable media with instructions stored thereon, the instructions comprising:
instructions for retrieving data related to a hearing prosthesis recipient's dynamic sound perception range;
instructions for determining configuration settings from the dynamic sound perception range, wherein the configuration settings define a relationship between an input signal and an output signal that is perceived as sound by the recipient, and wherein the relationship includes first, second, and third regions that each include different relationships between the input signal and the output signal, wherein the third region is defined by a ratio between the input signal and the output signal that is less than 1:1, and wherein the second region is defined by a ratio between the input signal and the output signal that is substantially 1:1 and by a gain value calculated by averaging a threshold hearing level and an uncomfortable loudness level and subtracting a normal speaking sound level from the average; and
instructions for providing the configuration settings for use by the hearing prosthesis, wherein the hearing prosthesis is configured to utilize the configuration settings to convert an audio input into an output signal that is delivered through the hearing prosthesis to be perceived as sound by a recipient of the hearing prosthesis.

17. The article of manufacture of claim 16, wherein the first region is limited to an output defined by an upper threshold of the dynamic sound perception range minus a correction value between 3 dB and 12 dB.

18. The article of manufacture of claim 16, wherein the configuration settings further include a fourth region between the first and second regions, and wherein the fourth region is defined by a ratio between the input signal and the output signal that is greater than 1:1.

* * * * *